United States Patent
Santala

(10) Patent No.: US 11,278,243 B2
(45) Date of Patent: Mar. 22, 2022

(54) REPOSITIONABLE SURFACE ELECTRODES

(71) Applicant: General Electric Company, Schenectady, NY (US)

(72) Inventor: Robert Filip Arnold Santala, Helsinki (FI)

(73) Assignee: General Electric Company, Schenectady, NY (US)

( * ) Notice: Subject to any disclaimer, the term of this patent is extended or adjusted under 35 U.S.C. 154(b) by 709 days.

(21) Appl. No.: 15/981,426

(22) Filed: May 16, 2018

(65) Prior Publication Data

US 2019/0350525 A1    Nov. 21, 2019

(51) Int. Cl.
*A61B 5/00* (2006.01)
*A61L 31/06* (2006.01)
*A61B 5/259* (2021.01)

(52) U.S. Cl.
CPC ............ *A61B 5/6832* (2013.01); *A61B 5/259* (2021.01); *A61B 5/68335* (2017.08); *A61L 31/06* (2013.01); *A61B 2562/0215* (2017.08)

(58) Field of Classification Search
CPC .............. A61B 5/6832; A61B 5/68335; A61B 5/04087; A61B 2562/0215; A61B 5/6833; A61B 5/08; A61B 2562/125; A61B 2562/164; A61B 5/04085; A61L 31/06
USPC ........................................................ 600/392
See application file for complete search history.

(56) References Cited

U.S. PATENT DOCUMENTS

| 4,515,162 A | * | 5/1985 | Yamamoto | ......... | A61B 5/04087 |
|---|---|---|---|---|---|
| | | | | | 600/391 |
| 6,377,845 B1 | | 4/2002 | Kinast | | |
| 6,415,169 B1 | * | 7/2002 | Kornrumpf | ........ | A61B 5/04085 |
| | | | | | 600/382 |

(Continued)

FOREIGN PATENT DOCUMENTS

| EP | 1359842 B1 | 5/2009 |
|---|---|---|
| EP | 2559280 A1 | 2/2013 |

(Continued)

OTHER PUBLICATIONS

Radius-7 brochure, Masimo, admitted prior art.

(Continued)

*Primary Examiner* — Linda C Dvorak
*Assistant Examiner* — Nils A Potter
(74) *Attorney, Agent, or Firm* — Andrus Intellectual Property Law, LLP

(57) ABSTRACT

A repositionable surface electrode for patient monitoring includes an active electrode layer having a top surface and a bottom surface and a leadwire connected to the active electrode layer. A first substrate has a top side, a bottom side, and a hole there through. The first substrate is positioned below the bottom surface of the active electrode layer such that the hole is aligned with the active electrode layer. An electrode gel channel is configured to conduct potentials from the patient's skin to the active electrode layer, the electrode gel channel extending through the hole in the first substrate. A silicone layer on the bottom side of the first substrate, avoiding the hole and the electrode channel, is configured to adhere the surface electrode to the patient's skin and to be removed from the patient's skin without becoming saturated with skin cells such that the electrode repositionable on the patient.

13 Claims, 5 Drawing Sheets

(56) References Cited

U.S. PATENT DOCUMENTS

| | | |
|---|---|---|
| 6,496,705 B1 | 12/2002 | Ng et al. |
| 6,749,566 B2 | 6/2004 | Russ |
| 7,390,299 B2 | 6/2008 | Weiner et al. |
| 8,475,368 B2 | 7/2013 | Tran et al. |
| 2004/0173003 A1 | 9/2004 | Ibane |
| 2006/0136768 A1 | 6/2006 | Liu et al. |
| 2006/0284621 A1 | 12/2006 | Doi |
| 2007/0299471 A1* | 12/2007 | Takahashi .......... A61B 5/04085 607/2 |
| 2008/0249390 A1* | 10/2008 | McIntire .............. A61B 5/0006 600/372 |
| 2008/0284599 A1 | 11/2008 | Zdeblick |
| 2009/0318818 A1 | 12/2009 | Whitaker et al. |
| 2010/0168605 A1 | 7/2010 | Aarts |
| 2011/0066051 A1 | 3/2011 | Moon |
| 2011/0145894 A1 | 6/2011 | Morchon et al. |
| 2012/0068855 A1 | 3/2012 | Matsumura |
| 2012/0108917 A1 | 5/2012 | Libbus et al. |
| 2013/0053674 A1 | 2/2013 | Volker |
| 2013/0109927 A1 | 5/2013 | Menzel |
| 2013/0281815 A1* | 10/2013 | Varadan ............. A61B 5/04085 600/388 |
| 2013/0289376 A1 | 10/2013 | Lang |
| 2013/0337842 A1 | 12/2013 | Wang et al. |
| 2014/0187883 A1 | 7/2014 | Lisogurski |
| 2015/0116130 A1 | 4/2015 | Grubis |
| 2015/0126834 A1* | 5/2015 | Wang ................... B32B 38/145 600/345 |
| 2016/0296135 A1* | 10/2016 | Yoo ...................... A61B 5/7225 |
| 2017/0139530 A1* | 5/2017 | Carpenter ............. G06F 3/0443 |
| 2017/0258402 A1* | 9/2017 | Acquista ................ H05K 1/189 |
| 2020/0054226 A1* | 2/2020 | Hung .................. A61B 5/0245 |

FOREIGN PATENT DOCUMENTS

| | | |
|---|---|---|
| EP | 1881784 B1 | 10/2013 |
| WO | 2014027273 A1 | 2/2014 |

OTHER PUBLICATIONS

IntelliVue Cableless Measurement brochure, Philips, Jun. 2013.

http://electronicdesign.com/power/lightning-bolts-defibrillators-and-protection-circuitry-save-lives.

Soundarapandian et al., "Analog Front-End Design for ECG Systems Using Delta-Sigma ADCs", Texas Instruments, SBAA160A, Mar. 2009, Revised Apr. 2010.

Torres, Bernat Albet., "Wireless System for the Measurement of Bioelectric Signals using Capacitive Electrodes", Universitat Politecnica de Catalunya.

\* cited by examiner

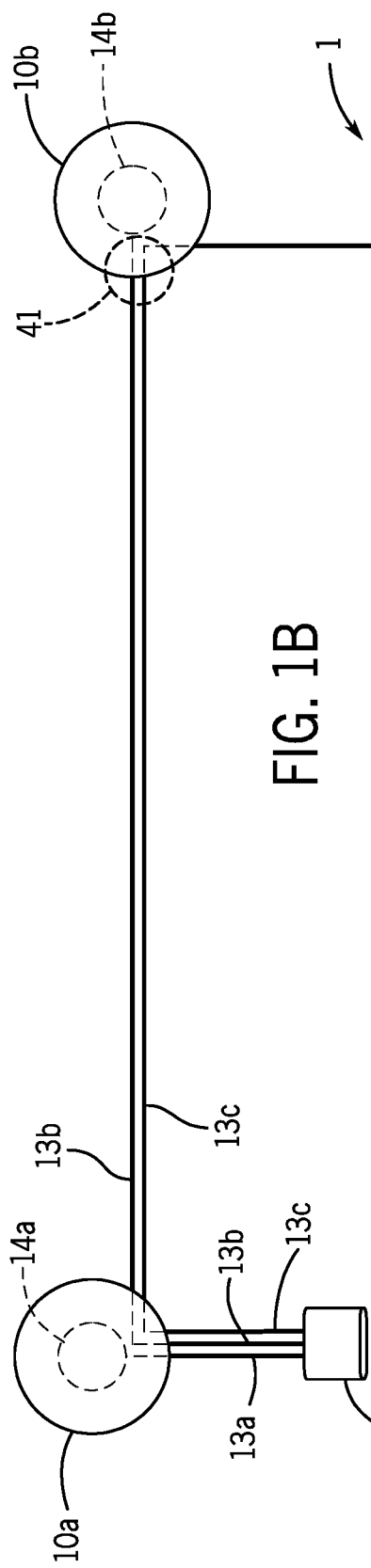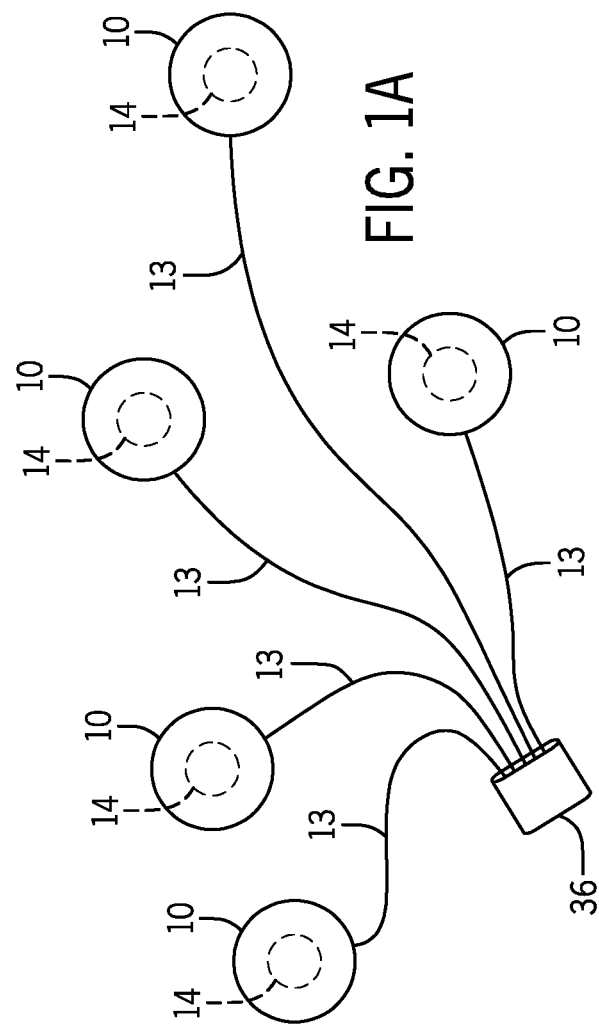

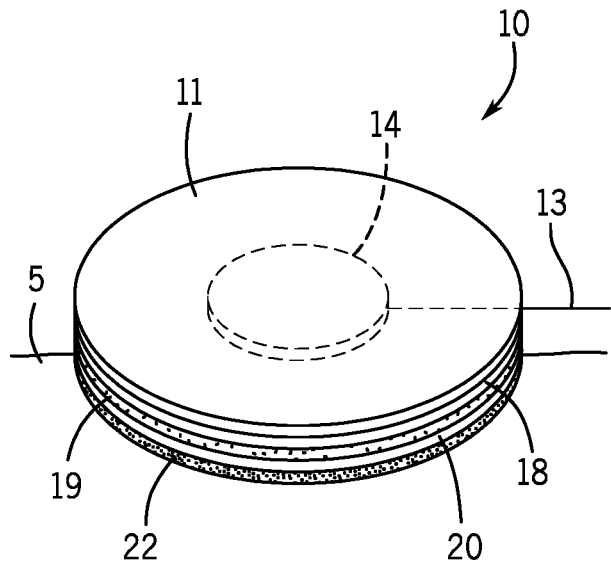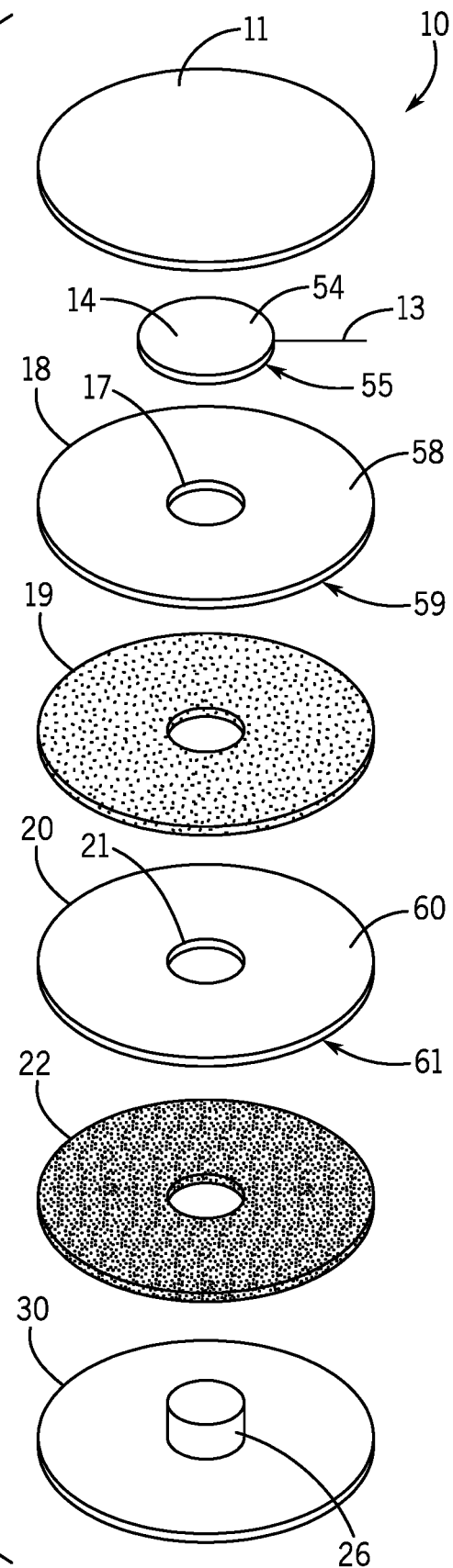

REPOSITIONABLE SURFACE ELECTRODES

BACKGROUND

The present disclosure generally relates to surface electrodes and surface electrode sets attachable to a patient's skin for physiological patient monitoring, and specifically to surface electrodes utilizing silicone-based adhesive that are repositionable on a patient's skin.

Surface electrodes, which are adhered to patient's skin surface, enable electrical contact between a patient's skin and a conductor. Surface electrodes generally connect between a patient and a physiological monitor monitoring a physiological condition of that patient, and the surface electrode provides the contact with the patient that enables measurement of potentials from the patient's body and conducts those potentials to the patient monitor. Thus, the surface electrodes are one of the key parts enabling physiological monitoring of biological signals, such as electrocardiograms (ECGs), electroencephalograms (EEGs), and respiration monitors, such as those that measure impedance across a patient's chest. Surface electrodes generally include an electrode plate or section of conductive material that is eclectically connected to the patient's skin. The electrode plate is also galvanically connected to a leadwire that conducts potentials from the electrode plate to a patient monitor. The electrode plate is typically connected to the patient's skin via a conductive paste or gel, generally referred to as an electrode gel.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a repositionable surface electrode of patient monitoring includes an active electrode layer having a top surface and a bottom surface and a leadwire connected to the active electrode layer. A first substrate has a top side, a bottom side, and a hole there through. The first substrate is positioned below the bottom surface of the active electrode layer such that the hole is aligned with the active electrode layer. An electrode gel channel is configured to conduct potentials from the patient's skin to the active electrode layer, the electrode gel channel extending through the hole in the first substrate. A silicone layer is on the bottom side of the first substrate, avoiding the hole and the electrode channel, which is configured to adhere the surface electrode to the patient's skin and to be removed from the patient's skin without becoming saturated with skin cells such that the electrode repositionable on the patient.

In one embodiment, a set of repositionable surface electrodes includes at least two surface electrodes. Each repositionable surface electrode includes a substrate having a top side, a bottom, and a hole. Each electrode further includes an active electrode layer having a top surface and a bottom surface, wherein the active electrode layer is positioned above the top side of the substrate and aligned with the hole. An electrode gel channel is provided and configured to conduct potentials from the patient's skin to the active electrode layer, wherein the electrode gel channel extends through the hole in the substrate. A silicone adhesive layer is provided on the bottom side of the substrate, avoiding the hole and the electrode gel channel, wherein the silicone adhesive layer is configured to adhere the surface electrode to the patient's skin and to be removed from the patient's skin without becoming saturated with skin cells such that the electrode is repositionable on the patient. The set of repositionable surface electrodes further includes a connector configured to connect the surface electrodes to a patient monitor so as to provide physiological potentials from the surface electrodes to the patient monitor. A first leadwire connects between the connector and the first electrode and a second leadwire connects between the connector and the second electrode.

In another embodiment, a set of repositionable surface electrodes includes a substrate and a connector attached to a connector end of the substrate. A surface electrode is formed on each of the electrode nodes, wherein each surface electrode includes an active electrode layer adhered to the substrate, an electrode gel channel configured to conduct potentials from a patient's skin to the active electrode layer, and a silicone adhesive layer on the bottom side of the substrate, avoiding the electrode gel channel. The silicone adhesive layer is configured to adhere the respective surface electrode to the patient's skin and to be removed from the patient's skin without becoming saturated with skin cells such that the respective surface electrode is repositionable on the patient. The set further includes a first leadwire connecting between the connector and the first electrode, a second leadwire connects between the connector and the second electrode, and a third leadwire connects between the connector and the third electrode.

Various other features, objects, and advantages of the invention will be made apparent from the following description taken together with the drawings.

BRIEF DESCRIPTION OF THE DRAWINGS

The present disclosure is described with reference to the following Figures.

FIG. 1A depicts one embodiment of a set of repositionable surface electrodes.

FIG. 1B depicts another embodiment of a set of repositionable surface electrodes.

FIGS. 2A and 2B depict one embodiment of a repositionable surface electrode.

DETAILED DESCRIPTION

Figure 3A:
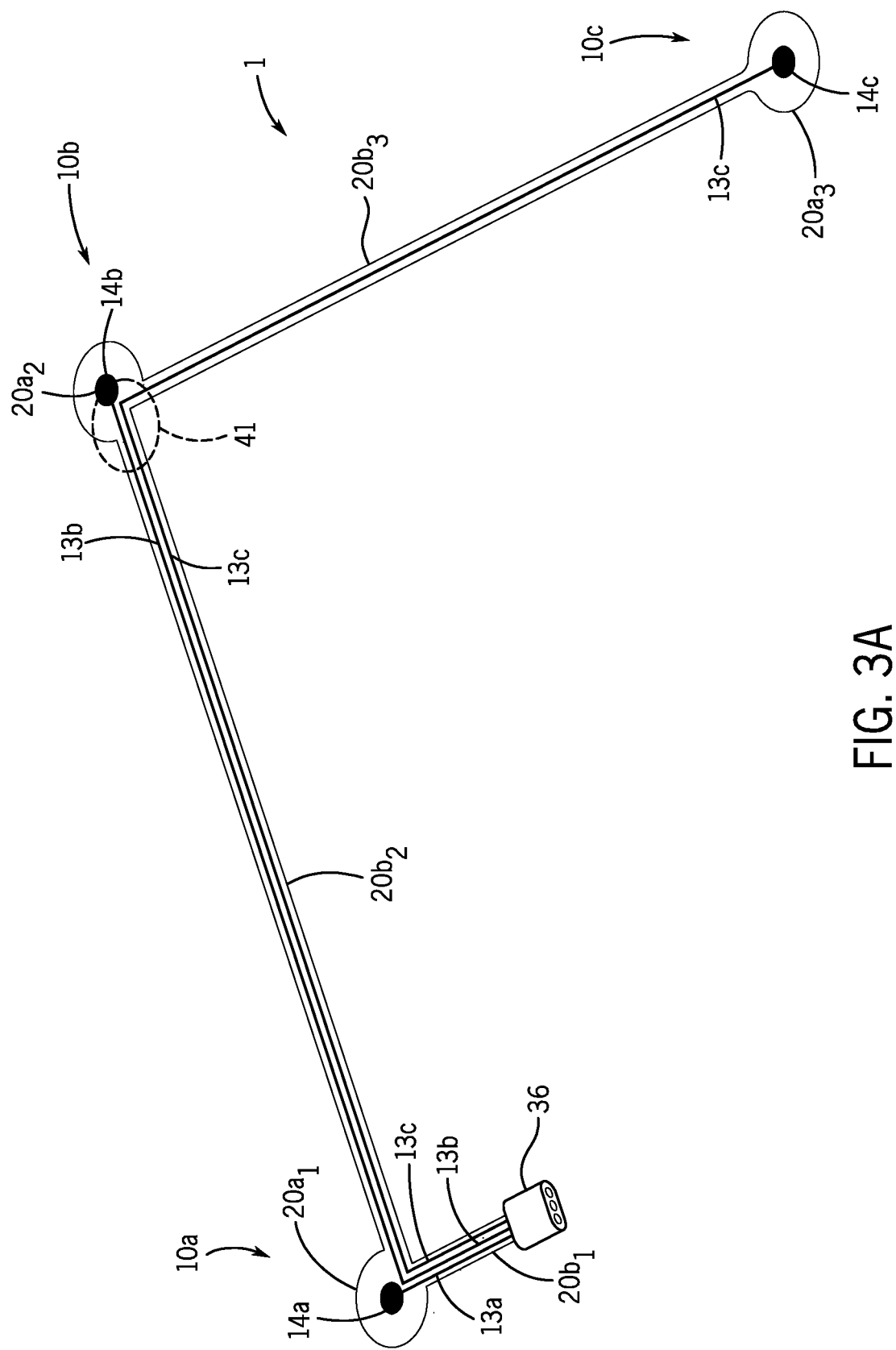
FIGS. 3A and 3B depict another embodiment of a set of repositionable surface electrodes.

The present inventor has recognized several problems with currently available patient electrodes and electrode sets. Standard surface electrodes, such as ECG electrodes, are attached to the skin with acrylic medical adhesives. Acrylic skin adhesives are generally configured for one-time application to a patient's skin and cannot be removed and reattached to the patient's skin in order to reposition an electrode. This is because acrylic skin adhesives adhere strongly to the skin and, upon removal, become saturated by dead skin cells peeled off of the skin when the acrylic skin adhesive is removed. The saturation by dead skin cells inhibits the acrylic skin adhesive from adhering well to the patient's skin a second time, and thus prevents reapplication of the same electrodes and prohibits repositioning and/or reuse of electrodes on a particular patient. While repositionable electrodes do currently exist, they are constructed using hydrogels as both an adhesive and an electric contact. Such hydrogels do not peel off dead skin cells, and thus allow for removal and reapplication of a particular electrode to a patient's skin. However, hydrogels are problematic between they are water-absorbing compounds. Thus, upon exposure to water, the hydrogels fail to maintain adhesion to the patient's skin and the electrodes between detected. This is problematic in many patient monitoring applications, including monitoring applications requiring extended monitoring periods. Sweat from the patient's skin and/or exposure to water by other means can inhibit adherence of the hydrogels to the patient's skin, and thus electrodes using hydrogels adhesives have a tendency to detach from the patient during the monitoring period.

Another challenge in the development of appropriate surface electrodes is adhesion time. Since acrylic adhesives become saturated when attached to the skin, the adhesion time is primarily based on the aggressively of the adhesive compound. However, strengthening the adhesion of an adhesive compound in order to increase adhesion time and allow for a longer patient monitoring duration means that long-lasting electrodes are very painful to remove. Aggressive acrylic adhesives may, depending on a patient's skin type and age, cause skin tears and open wounds when removed.

As described above, standard electrodes with acrylic adhesives are not repositionable due to saturation of the acrylic adhesive, and thus detached electrodes must be disposed of and new electrodes utilized. This is especially problematic if the electrode includes expensive hardware, and/or if the electrode comprises part of a unified set of electrodes and thus requires disposal of an entire electrode set when one electrode becomes detached. The inventor has recognized that in such situations, repositionability of an electrode is important to providing a useful and cost effective surface electrode for inclusion in a larger product (such as a wireless ECG sensor or monitoring system) and/or for inclusion in a set of surface electrodes. Furthermore, another problem recognized by the inventor is that current electrode sets are comprised of separate leads that must be individually arranged on the patient, which makes them difficult to apply accurately and prone to lead swapping and other errors.

The inventor has recognized that silicone-based adhesives can be utilized to solve the foregoing issues relating to surface electrodes. Silicone adhesive—i.e., adhesive compounds made on a siloxane base—are like elastomers and have a rubber-like appearance. The inventor has recognized that silicone adhesives can be used to provide a sufficient adhesive force to maintain an electrode on the patient's skin, while still having a gentle peel-off that allows removal of the electrode without risking causing skin wounds. Silicone adhesives are water tolerant and can be used during showering and washing. Importantly, the inventor has recognized that silicone adhesives do not adhere to patients' skin cells in the same way that acrylic adhesives do. Thus, unlike acrylic adhesives, silicone adhesives do not become saturated with dead skin cells upon removal from the patient's skin and thus continue to have the same or similar adhesive abilities even after removal. Accordingly, the inventor has recognized that silicone adhesives can be used to created repositionable electrodes, meaning that the electrode can be reattached to a patient if it has come off or been removed (partially or completely). Likewise, this allows the clinician to remove such a silicon adhesive electrode in order to check the skin condition beneath the electrode and can move the electrode to a new area if the skin at the previous attachment location has become irritated.

Furthermore, the inventor has further recognized that such repositionable electrodes can be more effectively combined into a unified set of electrodes, since removal of one electrode does not require disposal and replacement of the entire set. Thus, a set of electrodes can be provided that is designed for intuitive application to the patient, thus alleviating problems of misapplication, such as lead swapping. Moreover, since the electrodes can be repositioned, clinicians can move the electrodes during the monitoring process in order to optimize the recording of the physiological signals.

Figure 3B:
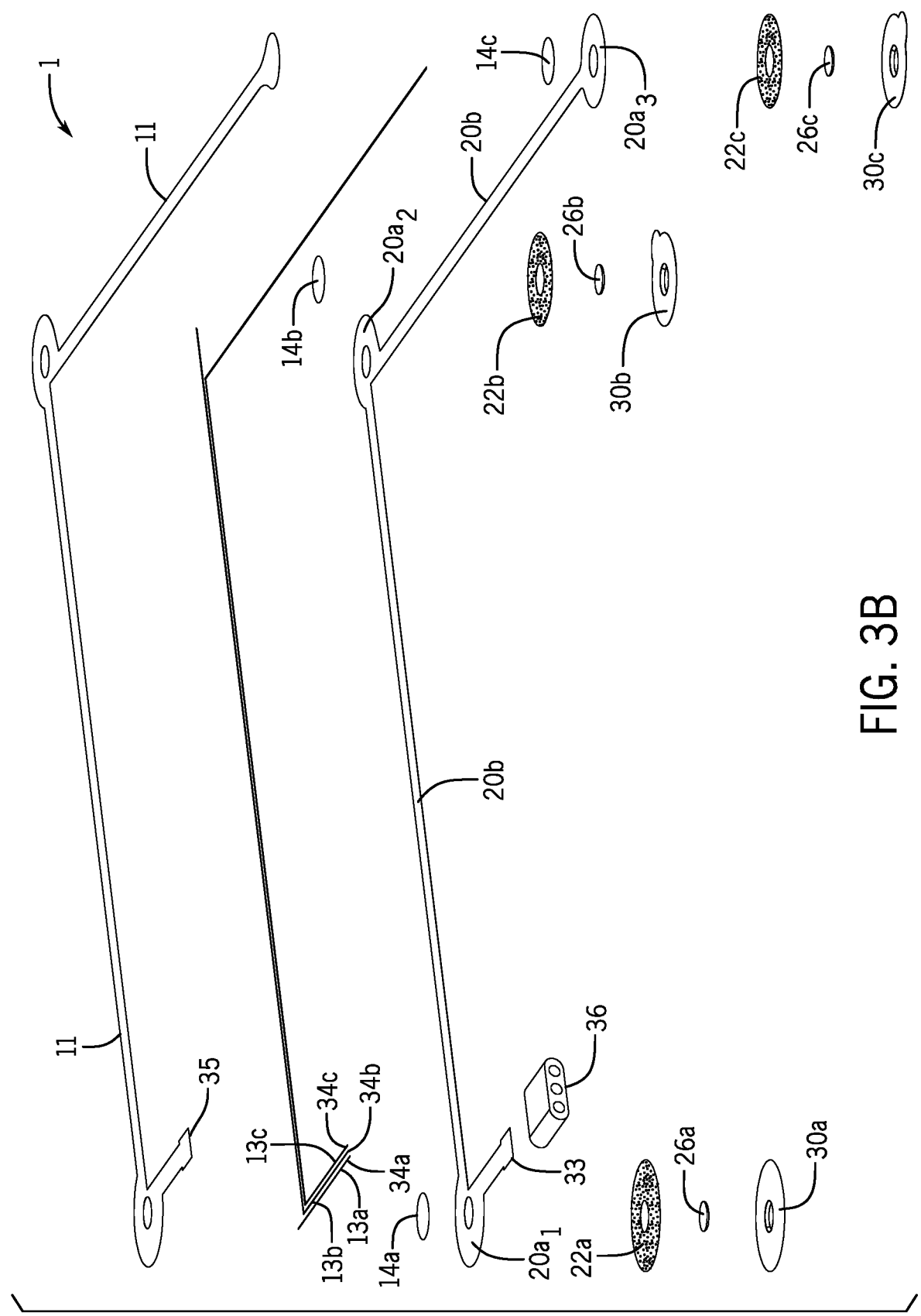
Figure 3C:
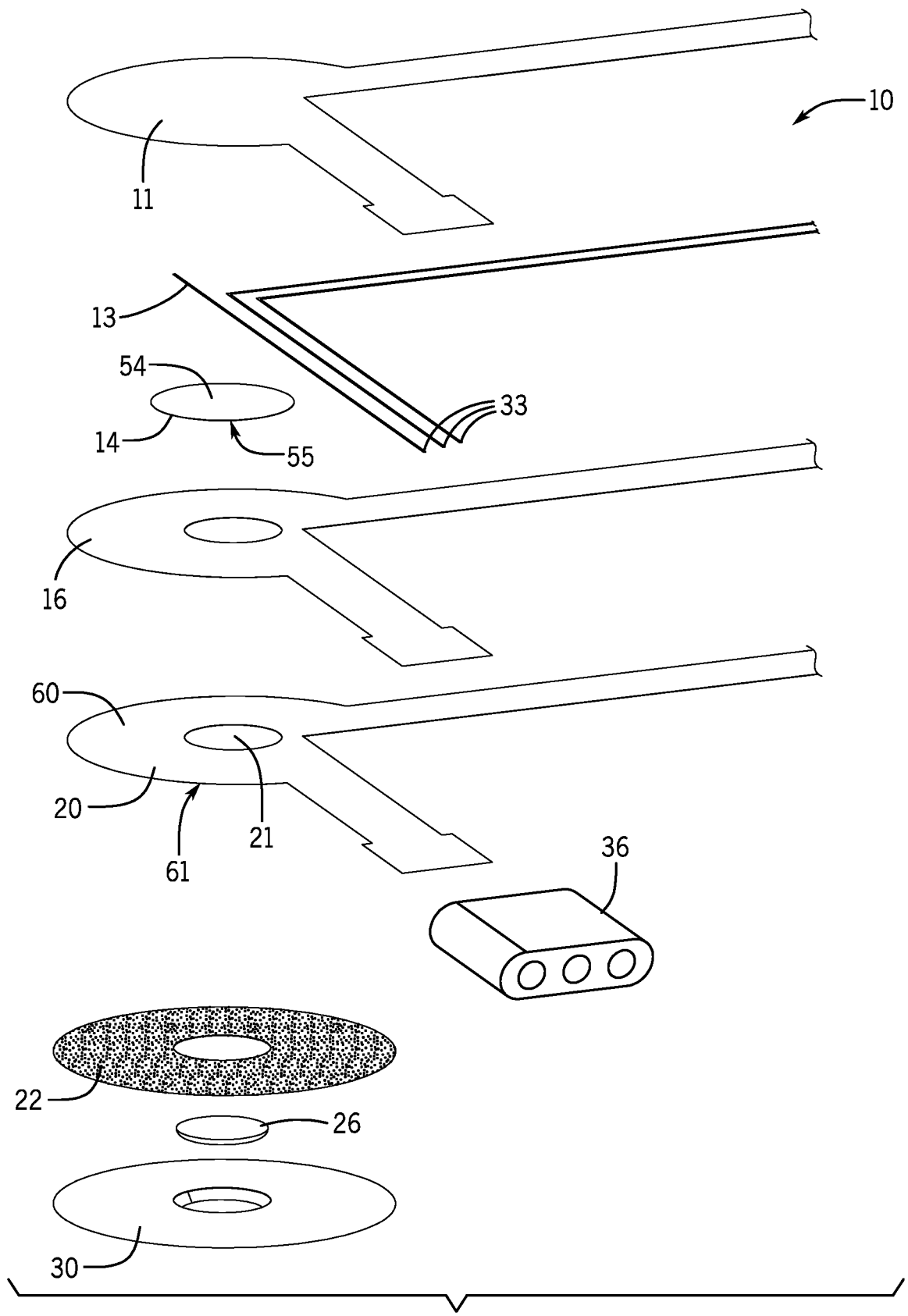
FIG. 3C depicts another embodiment of a repositionable surface electrode.

FIGS. 1A and 1B depict embodiments of a set 1 of repositionable surface electrodes 10. In various embodiments, the set 1 may include any number of two or more repositionable surface electrodes 10. In the example at FIG. 1A, set 1 of repositionable surface electrodes 10 includes 5 repositionable electrodes 10. In the example at FIG. 1B, the set 1 includes three repositionable surface electrodes 10*a*, 10*b*, and 10*c*. Referring also to FIGS. 2A, 2B, and 3C, each repositionable surface electrode includes a silicone adhesive layer configured to adhere the surface electrode 10 to a patient's skin. Each electrode 10 (e.g., 10*a*-10*c*) further includes an active electrode layer 14 galvanically connected to a leadwire 13. In the embodiment of FIG. 1B, each of the three electrodes 10*a*-10*c* includes an active electrode layer 14*a*-14*c* that connects to a respective leadwire 13*a*-13*c*. Each leadwire terminates at a connector 36 configured to connect to a patient monitor, thereby providing an electrical connection between each active electrode layer 14*a*-14*c* and the patient monitor.

As best illustrated in FIGS. 2B and 3C, embodiments of the repositionable surface electrode 10 are formed by a substrate 20 having a top side 60 and a bottom side 61, wherein the repositionable surface electrode 10 is formed around the top and bottom sides of the substrate 20. A hole 21 is provided in the substrate to allow conduction from the active electrode layer 14, which is provided adjacent to the substrate 20. In the depicted examples, the plate 14 is positioned above the substrate 20 such that the bottom surface 55 of the active electrode layer 14 is adjacent to the top side 60 of the substrate 20. In other embodiments, the active electrode layer 14 may be provided below the substrate 20, especially in printed embodiments, such as that depicted in FIG. 3C. An electrode gel channel 26 is configured to conduct potentials from the patient's skin 5 to the active electrode layer 14. As will be understood by a person having ordinary skill in the art in light of this disclosure, the electrode gel channel 26 may include a sponge which suspends and maintains the electrode gel within the channel. In certain embodiments, the active electrode layer 14 may be a hard metal-containing plate, such as a disk comprising silver, silver/silver-chloride or nickel-silver. In other embodiments, the active electrode layer 14 may be a flexible conductive substrate, such as a printed active electrode layer comprised of silver or silver/silver-chloride ink. In embodiments where the active electrode layer 14 is above the substrate 20, the electrode gel channel 26 extends from the bottom surface 55 of the active electrode layer 14, through the substrate 20 and to the bottom edge of the surface electrode such that it is configured to touch the patient's skin 5 when the surface electrode 10 is attached to the patient. Accordingly, a hole 21 is provided through the substrate, and any other layer between the plate 14 and the patient's skin 5 so as to form a channel filled by the electrode gel that provides conduction between the patient's skin 5 and the active electrode layer 14.

The silicone adhesive layer 22 is provided on the bottom side 61 of the first substrate 20. The silicone adhesive layer 22 is applied to avoid the hole 21 in the substrate 20, and thus the electrode gel channel 26 such that the electrode gel (once applied) is able to make direct contact between the active electrode layer 14 and the patient's skin 5. The silicone adhesive layer 22 is configured to adhere the surface electrode 10 to the patient's skin 5, and to be removed from the patient's skin without becoming saturated with skin cells such that the electrode is repositionable on the patient. For example, the silicone adhesive layer 22 may be comprised of a brush-on or roll-on liquid or semi-liquid silicone adhesive applied to the substrate 20. To provide just one example, the silicone adhesive layer 22 may be comprised of Uro-Bond® brush-on silicone adhesive by Urocare Products, Inc. of Pomona, Calif., such as product #500003 Uro-Bond III adhesive, which is a brush-on, pressure sensitive silicone adhesive.

FIGS. 2A and 2B depict an embodiment of a repositionable surface electrode 10 comprised of multiple layers assembled together in order to form the repositionable surface electrode 10. FIG. 2A schematically depicts an assembled repositionable surface electrode 10 adhered to a patient's skin 5. FIG. 2B depicts an exploded view of the assembled repositionable surface electrode 10, showing each layer thereof. FIGS. 3A-3C depict another embodiment comprising a repositionable surface electrode 10 manufactured by printing the various layers onto the top surface 54 and bottom surface 55 of the substrate 20. Specifically, FIGS. 3A and 3B depict one embodiment of a printed set 1 of repositionable surface electrodes 10a-10c, and FIG. 3C depicts an exploded view of one of the repositionable surface electrodes 10 in the set 1.

In the embodiment depicted in FIGS. 2A and 2B, the surface electrode 10 comprises two substrate layers, including a first substrate 20 on which the silicone adhesive layer 22 is applied, and a second substrate 18 on which another adhesive layer 19 is applied, such as an acrylic adhesive layer. In other embodiments, the adhesive layer 19 may be a different type of adhesive other than acrylic. Thus, this embodiment of the repositionable surface electrode 10 includes two substrate layers 20, 18 and two adhesive layers 22, 19 stacked on top of one another. As shown in the exploded view of FIG. 2B, the active electrode layer 14 has a top surface 54 and bottom surface 55. In the depicted embodiment, the active electrode layer 14 is positioned above the second substrate, such that the bottom surface 55 of the active electrode layer 14 adheres to the top side 58 of the second substrate 18. The second substrate has a hole 17 there through to enable the electrode gel channel 26 to contact the bottom surface 55 of the active electrode layer 14. In other embodiments, the active electrode layer 14 may be provided on a bottom side 59 of the second substrate 18. For example, the top surface 54 of the active electrode layer 14 may be adhered to the bottom side 59 of the second substrate 18, such as with an adhesive that does not react with the conductive metal of the active electrode layer 14. For example, the active electrode layer 14 may be a silver/silver chloride active electrode layer. An acrylic adhesive layer 19 may be provided beneath the active electrode layer 14 and on the bottom side 59 of the second substrate 18. The adhesive layer 19 is configured to avoid the electrode gel channel 26. The first substrate 20 is adhered to the acrylic adhesive layer 19. Specifically, the top side 60 of the first substrate 20 contacts the acrylic adhesive layer 19, and the first substrate 20 is positioned such that the hole 21 aligns with that in the acrylic adhesive layer 19 and the hole 17 and second substrate 18, such that a continuous channel is provided. The silicone adhesive layer 22 is provided on the bottom side 61 of the first substrate 20, also avoiding the hole 21 so as to continue the channel that forms the cavity for the electrode gel channel 26. The electrode gel channel 26 runs through the cavity formed by the holes in the respective layers so as to enable contact between the patient's skin 5 and the active electrode layer 14.

In certain embodiments, a release liner 30 is adhered to the silicone adhesive layer 22 to protect the silicone adhesive and the adhesive from the time of manufacture to the time of application to the patient's skin 5. The repositionable surface electrode 10 may further comprise a top layer 11 and/or other additional layers or elements applied over the second substrate 18 and the active electrode layer 14. For example, the top layer 11 may be a plastic material, such as a thermoplastic polyurethane (TPU) sheet sized to cover the second substrate 18. The top layer 11 may be adhered to the second substrate 18, such as with an adhesive applied to the top side 58 of the second substrate 18 or the bottom of the top layer 11.

FIG. 3C depicts another embodiment of a repositionable surface electrode 10 comprising just one substrate 20 on which the repositionable surface electrode 10 is built. In the depicted example, the active electrode layer 14 and the leadwires 13 are printed on a top side 60 of the substrate 20. Specifically, the active electrode layer 14 is printed on the top side 60 of the substrate 20, including over the hole 21 using a conductive ink, such as a silver/silver chloride ink. The leadwire 13 is also printed on the substrate 20, and is printed such that it makes a galvanic connection with the printed active electrode layer 14. In other embodiments, the active electrode layer 14 and/or leadwire(s) may be printed elsewhere on the substrate 20, such as on the bottom side 61. The silicone adhesive layer 22 is then applied to the bottom side 61 of the substrate 20, such as by brushing on or rolling on a liquid or semi-liquid silicone adhesive as described above. The electrode gel channel 26 is formed by inserting electrode gel through the hole 21 in the substrate 20 to contact the active electrode layer 14. A release liner 30 is also provided below the silicone adhesive layer 22 and the electrode gel channel 26 so as to protect the substances until the time of application to the patient's skin 5.

It will be understood by a person having ordinary skill in the art in view of this disclosure that, in certain embodiments, additional layers may be provided between the substrate 20 and the active electrode layer 14. Likewise, additional layers or elements may be provided on top of the substrate and/or the active electrode layer 14 and/or leadwires 13. In certain embodiments, the repositionable surface electrode 10 may further comprise a top layer 11 adhered to the substrate 20, and thus adhered over and protecting the printed active electrode layer 14 and printed leadwire(s) 13. For example, the top layer 11 may be a TPU sheet of the same shape and size as the substrate 20.

As described above, repositionability of an electrode is especially important in systems where expensive electronics are connected to the surface electrode and/or where the surface electrode comprises part of a unified electrode set. FIGS. 3A and 3B depict an exemplary embodiment of an electrode set 1 comprising printed active electrode layers 14 and leadwires 13. In the depicted embodiment, the substrate 20, such as comprised of a TPU sheet, forms electrode nodes 20a on which the electrodes are created, and bridging strips 20b connecting between the electrode nodes 20a and/or between the electrode nodes 20a and the connector 36.

Referring to FIGS. 3A and 3B, the depicted set 1 includes three repositionable electrodes 10a, 10b, 10c. Each repositionable electrode 10 is formed on a respective electrode node 20a of the substrate 20, including a first electrode node $20a_1$, a second electrode node $20a_2$, and a third electrode node $20a_3$. A leadwire 13a-13c is also printed on the substrate 20 so as to connect between a connector 36, such as that connects to a patient monitor, and a respective active electrode layer 14a-14c. In the depicted embodiments, the substrate 20, and thus the set 1 of repositionable electrodes 10a-10c, forms an L-shape. In the depicted embodiment, the connector 36 is located near the first repositionable electrode 10a, and thus all of the leadwires 13a, 13b, and 13c have a connection end 34a, 34b, 34c that is the termination location for the leadwire inside the connector 36 and provides the electrical connection point to the circuitry of patient monitor or other signal processing elements. In other embodiments, the connector 36 may be in any position with respect to the electrodes 10. Likewise, the substrate 20 may be configured differently to provide a different configuration of electrode nodes 20a and/or bridging strips 20b. For example, a bridging strip may connect directly between each electrode node 20a and the connector 36. In still other embodiments, the substrate may be a large patch, with electrode nodes 20a formed at various locations on the patch according to the patient monitoring needs.

As is shown most clearly in FIG. 3A, the depicted embodiment has the first leadwire 13a printed on a first bridging strip $20b_1$ between the connector 36 and the first electrode node $20a_1$. The second and third printed leadwires 13b, 13c also run on the first bridging strip $20b_1$ with all three leadwires 13a, 13b, 13c running parallel on the first bridging strip $20b_1$. The leadwires then diverge at the first electrode node $20a_1$, with the first leadwire 13a running directly to the first active electrode layer 14a and the second and third leadwires 13b and 13c being printed around, but not contacting, the first active electrode layer 14a. The second and third printed leadwires 13b, 13c run parallel and adjacent to one another along a second bridging strip $20b_2$, which connects and runs between the first electrode node $20a_1$ and the second electrode node $20a_2$ of the substrate 20. The second and third leadwires 13b and 13c run parallel until a branching point 41, where the second leadwire 13b branches toward the second active electrode layer 14b and the third leadwire 13c branches toward the third active electrode layer 14c. In the depicted embodiment, the second leadwire 13b and the third leadwire 13c branch and become perpendicular at the branching point 41. Depending on the particular configuration and shape of set 1 embodiment, the branching point 41 may be provided proximal or adjacent to, or even on, the second electrode node $20a_2$. The third leadwire 13c then continues on to contact the third active electrode layer 14c. Thus, the leadwires 13 each have different lengths, wherein the third leadwire 13c is longer than the second leadwire 13b, and the second leadwire 13b is longer than the first leadwire 13a.

As shown most clearly in FIG. 3B, the set 1 may further comprise a top layer 11 sized identically to the substrate 20, and thus configured to form a top layer over the entirety of the substrate 20, including the electrode nodes $20a_1$-$20a_3$ and the bridging strips $20b_1$-$20b_3$. In certain embodiments, the silicone adhesive 22 is applied only at and near the electrode nodes $20a_1$-$20a_3$. In certain embodiments, the silicone adhesive may be applied only to the bottom side 61 of the substrate 20 at each respective electrode node 20a. In other embodiments, the silicone adhesive may extend onto a portion of one or more bridging strips 20b, such as to provide additional support and adhesion for the electrodes 10 and to resist accidental snagging or pulling on the bridging strip 20b. In the embodiment depicted in FIG. 3B, for example, each electrode node $20a_1$-$20a_3$ has a silicone adhesive layer 22a, 22b, 22c. Each respective silicone adhesive layer 22a-22c may further extend onto a portion of the adjacent bridging strip(s) 20b, or may extend across the entire bottom side 61 of the substrate 20. A release liner 30a-30c of corresponding shape is provided to protect the silicone adhesive layer 22a-22c.

In other embodiments, the set 1 of repositionable surface electrodes 10a-10c may be comprised of separately manufactured repositionable electrodes 10, such as that depicted and described with respect to FIGS. 2A and 2B. In certain embodiments, the separate repositionable surface electrodes 10 are then connected with leadwires 13 to form an electrode set 1. FIGS. 1A and 1B depict are exemplary embodiments wherein separate insulated leadwires, such as copper leadwires, connect between the respective electrodes 10a, 10b, and 10c and the connector 36. Specifically in FIG. 1A, each leadwire 13 connects between the connector 36 and a respective repositionable electrode 10. FIG. 1B, a first leadwire 13a connects between the connector 36 and the first active electrode layer 14a. Second and third leadwires 13b and 13c travel to the first electrode 10a and may be adhered thereto. The second and third leadwires 13b and 13c then run parallel between the first repositionable electrode 10a and the second repositionable electrode 10b. At the second repositionable electrode 10b, a branching point 41 is provided where the second leadwire 13b branches to the second active electrode layer 14b and the third leadwire 13c branches perpendicularly and continues to the third surface electrode 10c.

It will be understood by a person having ordinary skill in the art in light of this disclosure that any number of two or more electrodes may be included in the set one. Moreover, the depicted embodiments provide the electrode set 1 arranged in an L-shape, which exemplifies one shape that is conducive to certain arrangements of chest electrodes, such as for three-lead ECG monitoring and/or respiration monitoring. In other embodiments, different numbers of electrodes may be provided, such as 2, 5, 6, and 10 electrodes, and in any appropriate configuration for a particular monitoring application. To provide just one example, the set 1 may comprise ten repositionable electrodes 10 arranged to provide a twelve-lead ECG recording from a patient. Other electrode arrangements are well known in the art and a set 1 may be created to conform to any such electrode arrangement. The connector 36 is configured to provide separate connection points for each leadwire 13 in the set 1, and thus the connector 36 is configured appropriately to provide connection to a patient monitor.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A set of repositionable surface electrodes comprising:
   at least a first repositionable electrode, a second repositionable electrode, and a third repositionable electrode each comprising:
   a substrate having a top side, a bottom side, and a hole;
   an active electrode layer having a top surface and a bottom surface, the active electrode layer positioned above the top side of the substrate and aligned with the hole;
   an electrode gel channel configured to conduct potentials from a patient's skin to the active electrode layer, the electrode gel channel extending through the hole in the substrate;
   a silicon adhesive layer on the bottom side of the substrate avoiding the hole and the electrode gel channel, the silicon adhesive layer configured to adhere the surface electrode to the patient's skin and to be removed from the patient's skin without becoming saturated with skin cells such that the electrode is repositionable on the patient;
   a connector configured to connect to a patient monitor so as to provide physiological potentials from the repositionable surface electrodes to the patient monitor;
   a first leadwire connecting between the connector and the first electrode;
   a second leadwire connecting between the connector and the second electrode;
   a third leadwire connecting between the connector and the third electrode; and
   wherein the second and third leadwires run adjacent and parallel between a first branch point proximal to the first electrode and a second branch point located between the first electrode and the second electrode.

2. The set of repositionable surface electrodes of claim 1, wherein the first, second, and third electrodes and leadwires are arranged in an L shape, wherein the second branch point is proximal to the second electrode at which the second leadwire runs to the second electrode and the third leadwire branches perpendicular to the second leadwire and runs to the third electrode.

3. The set of repositionable surface electrodes of claim 1, wherein the second branch point is proximal to the second electrode at which the second leadwire runs to the second electrode and the third leadwire runs to the third electrode.

4. The set of repositionable surface electrodes of claim 3, wherein at the first branch point the first leadwire runs to the first electrode and the second and third leadwires branch substantially perpendicular from the first leadwire.

5. A set of repositionable surface electrodes comprising:
   a substrate;
   a connector attached to a connection end of the substrate;
   the substrate forming a first electrode node, a second electrode node, and a third electrode node;
   a surface electrode formed on each of the electrode nodes, wherein each surface electrode comprises:
   an active electrode layer adhered to the substrate;
   an electrode gel channel configured to conduct potentials from a patient's skin to the active electrode layer;
   a silicon adhesive layer on a bottom side of the substrate avoiding the electrode gel channel, the silicon adhesive layer configured to adhere the respective surface electrode to the patient's skin and to be removed from the patient's skin without becoming saturated with skin cells such that the respective surface electrode is repositionable on the patient;
   a first leadwire connecting between the connector and the first surface electrode;
   a second leadwire connecting between the connector and the second surface electrode;
   a third leadwire connecting between the connector and the third surface electrode; and
   wherein the second and third leadwires run adjacent and parallel between a first branch point proximal to the first surface electrode and a second branch point located between the first surface electrode and the second surface electrode.

6. The set of repositionable surface electrodes of claim 5, wherein each active electrode layer is printed on the substrate at a respective substrate node with conductive ink, and the first, second and third leadwires are printed on the substrate with conductive ink.

7. The set of repositionable surface electrodes of claim 6, wherein each electrode node has a hole therethrough and the active electrode layer is printed on a top side of the substrate and over the hole, and wherein the electrode gel channel extends through the hole in the substrate.

8. The set of repositionable surface electrodes of claim 6, a top layer adhered to the substrate over the printed active electrode layer and printed leadwire.

9. The set of repositionable surface electrodes of claim 5, wherein the active electrode layer is a metal plate.

10. The set of repositionable surface electrodes of claim 5, wherein the first, second, and third surface electrodes and leadwires are arranged in an L shape, with the first electrode closest to the connector such that the first leadwire is shorter than the second and third lead wires and the third electrode is further from the connector such that the third leadwire is longer than the first and second leadwires.

11. The set of repositionable surface electrodes of claim 10, wherein the second branch point is proximal to the second surface electrode at which the second leadwire runs to the second surface electrode and the third leadwire branches perpendicular to the second leadwire and runs to the third surface electrode.

12. The set of repositionable surface electrodes of claim 5, wherein the branch point is proximal to the second electrode at which the second leadwire runs to the second electrode and the third leadwire runs to the third electrode.

13. The set of repositionable surface electrodes of claim 12, wherein at the first branch point the first leadwire runs to the first electrode and the second and third leadwires branch substantially perpendicular from the first leadwire.

* * * * *